US00PP30181P3

(12) United States Plant Patent
Suphachadiwong

(10) Patent No.: US PP30,181 P3
(45) Date of Patent: Feb. 5, 2019

(54) *SANSEVIERIA* PLANT NAMED 'SUPSAN1606'

(50) Latin Name: ***Sansevieria* hybrid**
Varietal Denomination: SUPSAN1606

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 15/732,596

(22) Filed: Nov. 30, 2017

(65) Prior Publication Data

US 2018/0160605 P1 Jun. 7, 2018

(30) Foreign Application Priority Data

Dec. 1, 2016 (QZ) ..... PBR 2016/3020

(51) Int. Cl.
*A01H 5/12* (2018.01)

(52) U.S. Cl.
USPC ..... Plt./382
CPC ..... *A01H 5/12* (2013.01)

(58) Field of Classification Search
USPC ..... Plt./382
See application file for complete search history.

*Primary Examiner* — Susan McCormick Ewoldt
(74) *Attorney, Agent, or Firm* — Samuel R. McCoy, Jr.

(57) ABSTRACT

A new and distinct *Sansevieria* plant named 'SUPSAN1606' which is characterized by the combination of a relatively large plant size with an outward growth habit and very broad orbicular plant form, long, linear succulent foliage with an outward attitude and significant spacing between individual leaves, terete foliage with numerous shallow axial grooves and a deeper central channel, dark green foliage with inconspicuous mottled radial bands which are slightly darker green, and the stability of all characteristics from generation to generation.

2 Drawing Sheets

Latin name of the genus and species: The Latin name of the genus and species of the novel variety disclosed herein is *Sansevieria* hybrid.

Variety denomination: The inventive variety of *Sansevieria* disclosed herein has been given the variety denomination 'SUPSAN1606'.

CROSS REFERENCE TO RELATED APPLICATIONS

This application claims priority to the Community Plant Variety Rights application number 2016/3020, filed Dec. 1, 2016, which is herein incorporated by reference.

BACKGROUND OF THE INVENTION

Parentage: The *Sansevieria* variety 'SUPSAN1606' originated as a seedling selection from the controlled pollination of the proprietary seed parent, *Sansevieria* hybrid 'MXJM1061' (not patented), with the proprietary pollen parent, *Sansevieria* hybrid 'MXJF1061' (not patented). Both parents were developed by, and are owned by, the inventor and were never commercially released. Said crossing was conducted by the inventor in a small, netted greenhouse in Chonburi, Thailand in December of 2009. Seeds from said cross were harvested, then germinated, and the resulting seedlings were grown to a mature size in order to evaluate for a desirable combination of commercial characteristics. In April of 2012, one candidate plant was observed to exhibit a unique growth habit and leaf coloration. After confirmation of the distinctness and stability of the characteristics first observed, the inventor selected the new *Sansevieria* cultivar, 'SUPSAN1606', for commercial introduction.

Asexual Reproduction: Asexual reproduction of 'SUPSAN1606' by way of harvesting vegetative ground shoots was first initiated in April of 2012 at Chonburi, Thailand. Access to all plants was restricted, as plants were kept in a greenhouse not open to the public. Through subsequent propagation of vegetative ground shoots, five generations have been reproduced which have shown that the unique features of this cultivar are stable and reproduced true to type.

SUMMARY OF THE INVENTION

The cultivar 'SUPSAN1606' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'SUPSAN1606'. These characteristics in combination distinguish 'SUPSAN1606' as a new and distinct *Sansevieria* cultivar:

1. *Sansevieria* 'SUPSAN1606' is a relatively large plant with an outward growth habit and very broad orbicular plant form; and
2. *Sansevieria* 'SUPSAN1606' exhibits long, linear succulent foliage with an outward attitude and significant spacing between individual leaves; and
3. *Sansevieria* 'SUPSAN1606' exhibits terete foliage with numerous shallow axial grooves and a deeper central channel; and 4. *Sansevieria* 'SUPSAN1606' exhibits dark green foliage with inconspicuous mottled radial bands which are slightly darker green.

BOTANICAL DESCRIPTION OF THE PLANT

Figure 1:
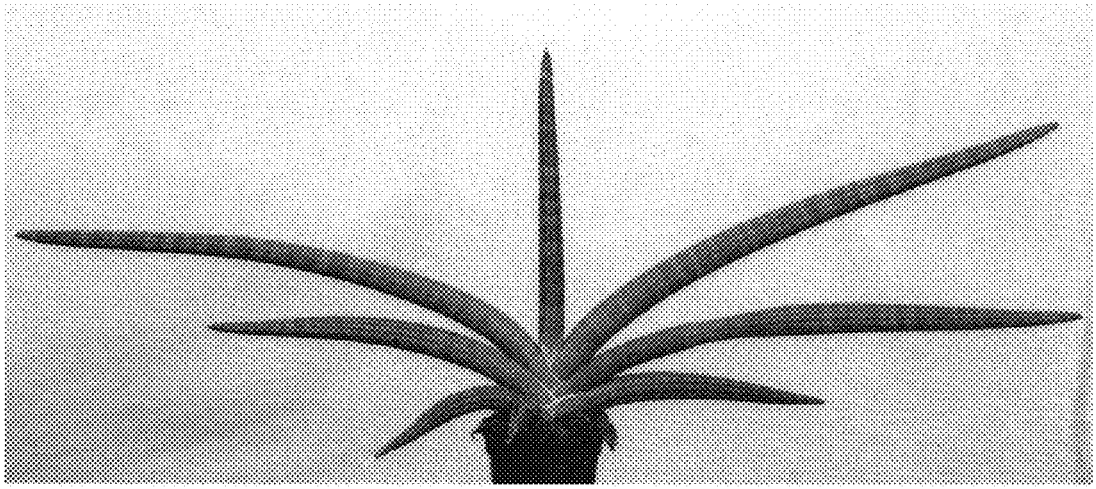
FIG. 1 illustrates, as nearly true as it is reasonably possible to make the same in color photographs of this type, an exemplary plant of 'SUPSAN1606' grown in a commercial greenhouse in Chonburi, Thailand. This plant is approximately 12 months old, shown planted in a 10 cm container.
Figure 2:
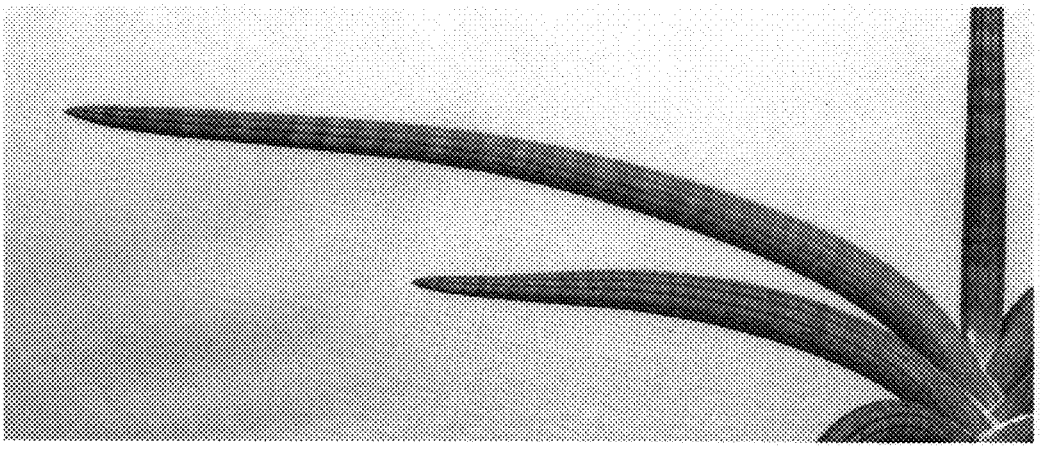
FIG. 2 illustrates, as nearly true as it is reasonably possible to make the same in color photographs of this type, the typical foliage of 'SUPSAN1606'.

The following observations and measurements, made in October of 2017, describe averages from a sample set of six specimens of 12 month old 'SUPSAN1606' plants grown in 10 cm containers, at a commercial greenhouse in Chonburi, Thailand. The plants were grown using conventional greenhouse production protocols for *Sansevieria* plants which consisted of overhead irrigation, 50% shade cloth, and no fertilizer. No photoperiodic or chemical treatments were given to the plants.

Those skilled in the art will appreciate that certain characteristics will vary with older or, conversely, with younger plants. 'SUPSAN1606' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SUPSAN1606' and comparisons with the parents and most similar commercial variety of *Sansevieria* are provided below.

Plant description:

*Growth habit*.—Monopodial perennial; equitant.

*Plant form*.—Vertically flattened, very broad flattened orbicular.

*Average height*.—32.5 cm.

*Plant spread*.—24.4 cm at the narrowest point, and 90.0 cm at the widest point.

*Plant vigor*.—Moderate.

*Growth rate*.—Moderate.

*Propagation type*.—Division of vegetative ground shoots; harvesting ground shoots from the mother plant.

*Propagation details*.—The time needed to root a shoot division is approximately 2 to 3 months with temperatures ranging from approximately 17 to 40 degrees Celsius.

*Disease resistance*.—Plants have not been observed to be susceptible or resistant to pathogens and pests common to *Sansevieria*.

*Environmental tolerances*.—Adapt to, at least, USDA Zones 10 and 12 and temperatures as high as 40 degrees Celsius; moderate tolerance to rain; moderate to high tolerance to wind.

Root system:

*General*.—Moderately dense and moderately branched rooting; roots are slightly fibrous.

*Distribution in the soil profile*.—Shallow to moderately deep.

*Diameter of roots*.—0.2 cm on average.

*Texture*.—Smooth; no root hairs.

*Color*.—Greyed-orange, nearest to RHS 165B.

Stem:

*Branching habit*.—Monopodial, equitant; decurrent leaf bases form the stem.

*Number of primary (main) stems per plant*.—One.

*Number of secondary (lateral) branches per plant*.—None.

*Appearance and shape*.—Stem is not visible; decurrent leaf bases form the stem.

*Length*.—The decurrent leaf bases collectively have an average length of 6.2 cm.

*Diameter*.—The decurrent leaf bases collectively have an average diameter of 2.3 cm.

*Internode length*.—0.9 cm.

Foliage:

*Arrangement*.—Distichous.

*Attachment*.—Decurrent.

*Division*.—Simple.

*Quantity*.—7.

*Attitude*.—At an average angle of 72.5 degrees to vertical.

*Lamina*.—Dimensions — 46.7 cm long and 2.3 cm wide. Thickness — Approximately 2.4 cm. Shape of blade — Narrowly linear in outline. Cross-section — Terete with numerous shallow axial grooves and a deeper central channel. Aspect — Slightly curved downward. Apex — Narrowly acute with a papery tip, which is colored greyed-white, nearest to RHS 156C. Base — Decurrent. Margin — Leaves are terete so there are no margins, with the exception of the leaf base; leaf base margins are entire. Texture of upper surface — Glabrous; smooth; succulent. Texture of lower surface — Glabrous; smooth; succulent. Luster of the upper surface — Matte. Luster of the lower surface — Matte. Color — Juvenile foliage, upper surface — Nearest to in between green, RHS NN137A, and yellow-green, RHS 147A, with mottled radial bands which are colored nearest to a mixture of yellow-green, RHS 147B, and greyed-green, RHS 191B. Juvenile foliage, lower surface — Nearest to in between green, RHS NN137A, and yellow-green, RHS 147A, with mottled radial bands which are colored nearest to a mixture of yellow-green, RHS 147B, and greyed-green, RHS 191B; base is yellow-green, nearest to RHS 144C. Mature foliage, upper surface — Nearest to in between green, RHS 137B, and yellow-green, RHS 147A, with mottled radial bands which are colored yellow-green, nearest to a mixture of RHS 147B and 147C. Mature foliage, lower surface — Nearest to in between green, RHS 137B, and yellow-green, RHS 147A, with mottled radial bands which are colored yellow-green, nearest to a mixture of RHS 147B and 147C; margins of the decurrent base are papery and translucent and colored greyed-white, nearest to RHS 156A. Venation — Pattern — Parallel. Color, upper surface — Nearest to in between green, RHS 139A, and yellow-green, RHS 147A, but slightly darker. Color, lower surface — Nearest to in between green, RHS 139A, and yellow-green, RHS 147A, but slightly darker.

*Petiole*.—No petioles present, leaves are decurrent. Inflorescence: No flowering has been observed to date.

Comparisons With the Parent Plants

Plants of the new cultivar 'SUPSAN1606' differ from the seed parent, *Sansevieria* hybrid 'MXJM1061' (not patented), by the characteristics described in Table 1.

TABLE 1

| Characteristic | 'SUPSAN1606' | 'MXJM1061' |
|---|---|---|
| Plant size. | Larger than 'MXJM1061'. | Smaller than 'SUPSAN1606'. |
| Foliage cross section. | Terete with numerous shallow axial grooves and a deeper central channel. | Terete. |
| Foliage thickness. | Thicker. | Thinner. |
| Foliage texture. | Less smooth than 'MXJM1061'. | Smoother than 'SUPSAN1606'. |
| General coloration of the foliage. | Darker green closer to greyed-green. | Lighter green. |
| General coloration of the leaf venation. | Darker green. | Lighter green. |

Plants of the new cultivar 'SUPSAN1606' differ from the pollen parent, *Sansevieria* hybrid 'MXJF1061' (not patented), by the characteristics described in Table 2.

TABLE 2

| Characteristic | 'SUPSAN1606' | 'MXJF1061' |
|---|---|---|
| Plant size. | Larger than 'MXJF1061'. | Smaller than 'SUPSAN1606'. |
| Foliage length. | Longer than 'MXJF1061'. | Shorter than 'SUPSAN1606'. |

TABLE 2-continued

| Characteristic | 'SUPSAN1606' | 'MXJF1061' |
|---|---|---|
| Foliage thickness. | Thicker. | Thinner. |
| Foliage texture. | Smoother than 'MXJF1061'. | Less smooth than 'SUPSAN1606'. |
| General coloration of the foliage. | Darker green closer to greyed-green. | Greyed-green. |
| General coloration of the leaf venation. | Lighter green. | Darker green. |

Comparison With the Most Similar *Sansevieria* Cultivar Known to the Inventor Plants of the new cultivar 'SUPSAN1606' are most similar to the commercial cultivar, *Sansevieria cylindrica* 'SAN201202' (U.S. Plant Pat. No. 24,457). A comparison of 'SUPSAN1606' with 'SAN201202' is described in Table 3.

TABLE 3

| Characteristic | 'SUPSAN1606' | 'SAN201202' |
|---|---|---|
| Growth habit. | Less compact than 'SANS201202'. | More compact than 'SUPSAN1606'. |
| Foliage attitude. | More outward; greater spacing between individual leaves. | More upright; individual leaves are held more tightly together. |
| Leaf aspect. | Slightly curved downward. | Generally straight. |
| Foliage apex. | Narrowly acute. | Acute. |
| General coloration of the foliage. | Darker green closer to greyed-green. | Lighter green. |
| Prominence of the color pattern on the foliage. | Less prominent green mottled radial bands. | More prominent green mottled radial bands. |

That which is claimed is:

1. A new and distinct variety of *Sansevieria* plant named 'SUPSAN1606', substantially as described and illustrated herein.

* * * * *